(12) United States Patent
Budidet et al.

(10) Patent No.: US 9,573,965 B2
(45) Date of Patent: Feb. 21, 2017

(54) PROCESS FOR THE PREPARATION OF DOLUTEGRAVIR

(71) Applicant: Aurobindo Pharma Ltd, Hyderabad (IN)

(72) Inventors: Shankar Reddy Budidet, Hyderabad (IN); Nageshwar Dussa, Hyderabad (IN); Gowrisankar Rao Kaki, Hyderabad (IN); Srinivasa Rao Yatcherla, Hyderabad (IN); Jagan Mohan Reddy Sanapureddy, Hyderabad (IN); Subba Reddy Danda, Hyderabad (IN); Srinivasachary Katuroju, Hyderabad (IN); Sivakumaran Meenakshisunderam, Hyderabad (IN)

(73) Assignee: Aurobindo Pharma Ltd, Hyderabad (IN)

( * ) Notice: Subject to any disclaimer, the term of this patent is extended or adjusted under 35 U.S.C. 154(b) by 0 days.

(21) Appl. No.: 14/888,702

(22) PCT Filed: Feb. 7, 2014

(86) PCT No.: PCT/IB2014/000149
§ 371 (c)(1),
(2) Date: Nov. 2, 2015

(87) PCT Pub. No.: WO2014/128545
PCT Pub. Date: Aug. 28, 2014

(65) Prior Publication Data
US 2016/0108058 A1    Apr. 21, 2016

(30) Foreign Application Priority Data

Feb. 19, 2013 (IN) .............................. 725/CHE/2013
Mar. 27, 2013 (IN) ........................... 1361/CHE/2013

(51) Int. Cl.
| C07D 498/14 | (2006.01) |
| C07C 213/08 | (2006.01) |
| C07C 215/08 | (2006.01) |
| C07C 213/02 | (2006.01) |
| C07C 213/10 | (2006.01) |
| C07C 59/255 | (2006.01) |

(52) U.S. Cl.
CPC ........... *C07D 498/14* (2013.01); *C07C 59/255* (2013.01); *C07C 213/02* (2013.01); *C07C 213/08* (2013.01); *C07C 213/10* (2013.01); *C07C 215/08* (2013.01)

(58) Field of Classification Search
CPC ..... C07D 498/14; C07C 59/25; C07C 215/08; C07C 213/08
USPC ............................................ 544/95; 562/590
See application file for complete search history.

(56) References Cited

U.S. PATENT DOCUMENTS

| 5,696,270 A * | 12/1997 | Kempf .................... C07C 69/65 548/202 |
| 8,236,991 B2 * | 8/2012 | Ambati ................. C07C 213/10 548/203 |
| 8,288,141 B2 * | 10/2012 | Savile .................. C12N 9/0006 435/122 |

* cited by examiner

*Primary Examiner* — Kahsay Habte
(74) *Attorney, Agent, or Firm* — Jay R Akhave

(57) ABSTRACT

The present invention provides (R)-3-Amino-1-butanol (D)-tartarate (IIb); process for its preparation and its conversion to Dolutegravir. The present invention also provides an improved process for the preparation of Dolutegravir (I) or pharmaceutically acceptable salts wherein compound (XVI) is reacted with an optically active acid addition salt of (R)-3-amino-1-butanol (IIa).

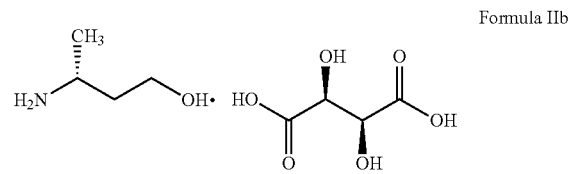

Formula IIb

10 Claims, No Drawings

PROCESS FOR THE PREPARATION OF DOLUTEGRAVIR

FIELD OF THE INVENTION

The present invention relates to an improved process for the preparation of Dolutegravir (I) or pharmaceutically acceptable salts thereof.

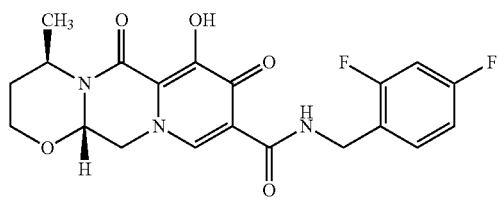

Formula I

The present invention also relates to an improved process for the preparation of (R)-3-amino-1-butanol (II).

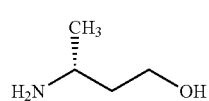

Formula II

The compound (II) is a key precursor in the preparation of integrase inhibitor, Dolutegravir (I).

BACKGROUND OF THE INVENTION

Dolutegravir (I) is chemically known as (4R,12aS)—N-[(2,4-difluorophenyl)methyl]-3,4,6,8,12,12a-hexahydro-7-hydroxy-4-methyl-6,8-dioxo-2H-pyrido[1',2':4,5]pyrazino[2,1-b][1,3]oxazine-9-carboxamide.

Dolutegravir is a human immunodeficiency virus type 1 (HIV-1) integrase strand transfer inhibitor (INSTI) indicated in combination with other antiretroviral agents for the treatment of HIV-1 infection. Dolutegravir is being marketed under the trade name Tivicay®.

U.S. Pat. No. 8,129,385 disclosed Dolutegravir or its pharmaceutically acceptable salts thereof.

US '385 also discloses a process for the preparation of Dolutegravir (I). The process involves the condensation of 5-benzyloxy-4-hydroxy-6-hydroxymethyl nicotinic acid (III) with 2,4-difluorobenzylamine (IV) to produce 5-benzyloxy-N-(2,4-difluorobenzyl)-4-hydroxy-6-hydroxymethyl nicotinic acid amide (V), which is further under goes oxidation using manganese dioxide ($MnO_2$) to produce 5-benzyloxy-N-(2,4-difluorobenzyl)-6-formyl-4-hydroxy-nicotinic acid amide (VI). This amide compound (VI) is reacted with sodium chlorite ($NaClO_2$) to produce 3-benzyloxy-5-(2,4-difluorobenzylcarbamoyl)-4-hydroxy-pyridine-2-carboxylic acid (VII), which is further treated with methanol (MeOH) to produce 3-benzyloxy-5-(2,4-difluorobenzyl)-4-hydroxy-pyridine-2-carboxylic acid methyl ester (VIII). The methyl ester compound (VIII) is reacted with 3-bromopropene to produce 1-allyl-3-benzyloxy-5-(2,4-difluorobenzyl)-4-oxo-1,4-dihydropyridine-2-carboxylic acid methyl ester (IX), which is further reacted with potassium osmate dihydrate ($K_2OsO_4.2H_2O$) to produce 3-benzyloxy-5-(2,4-difluorobenzylcarbamoyl)-4-oxo-1-(2-oxo-ethyl)-1,4-dihydropyridine-2-carboxylic acid methyl ester (X). The compound (X) is reacted with (R)-3-amino-1-butanol (II) to produce benzyloxy Dolutegravir (XI), which is deprotected by treating with TFA to produce Dolutegravir (I).

The Process is as Shown in Scheme-I Below:

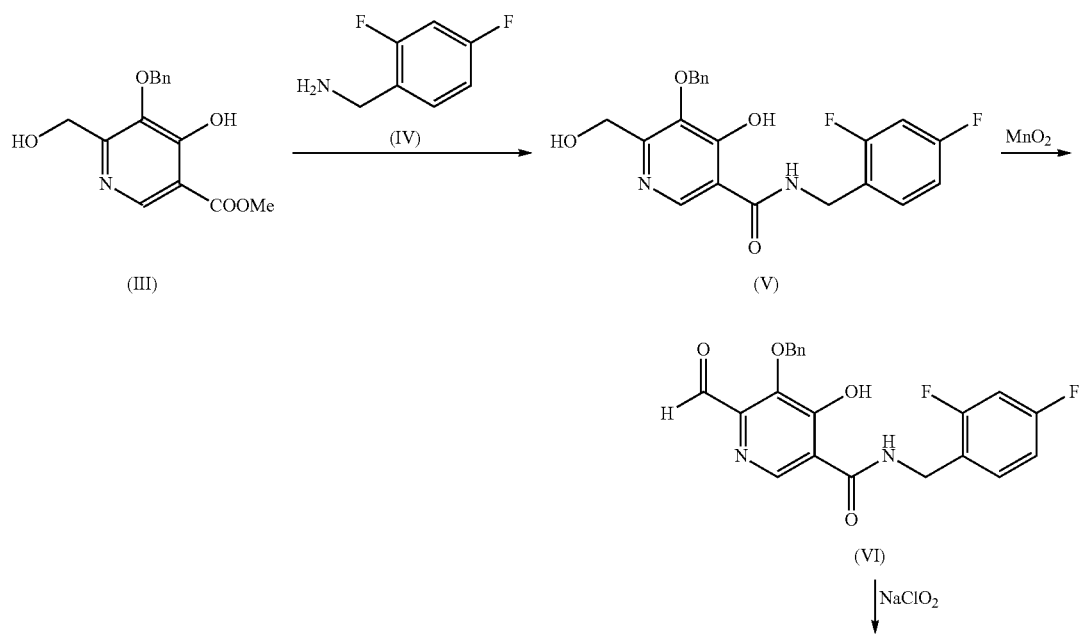

Scheme-I

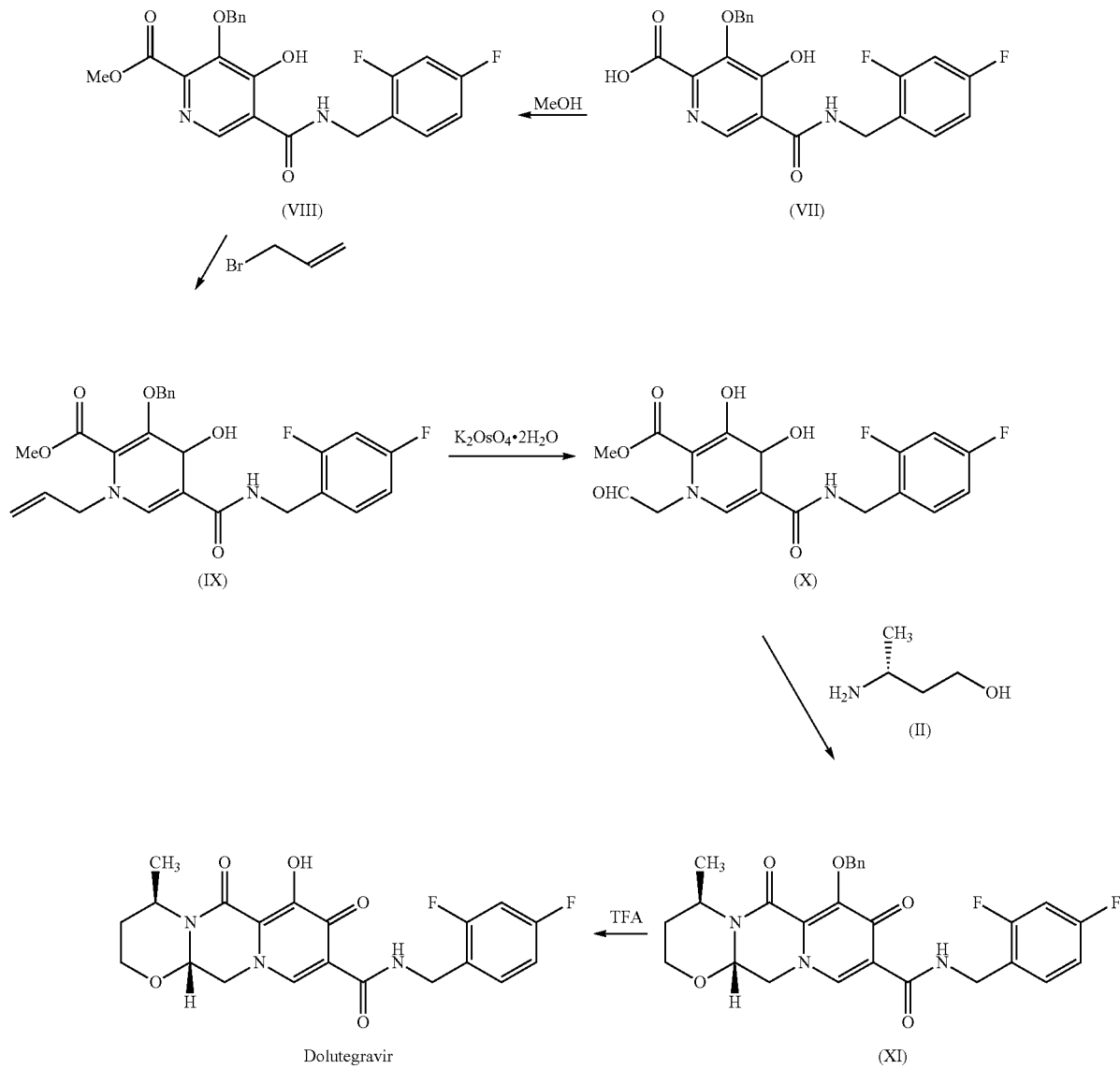

The major disadvantage with the above prior-art process is that it involves large no of steps and tedious work-up procedures to isolate the required product. This results a longer period of time cycle is required to produce Dolutegravir (I), which in turn renders the process more costly and less eco friendly. Further the above processes are low yielding and with less purity.

U.S. Pat. No. 8,217,034 discloses variant process for the preparation of Dolutegravir. This process involves the reaction of methyl 1-(2,2-dihydroxyethyl)-4-oxo-3-[(phenylmethyl)oxy]-1,4-dihydro-2-pyridine carboxylate (XII) with (R)-3-amino-1-butanol (II) to produce (4R,12aS)-4-methyl-7-[(phenylmethyl)oxy]-3,4,12,12a-tetrahydro-2H-pyrido[1',2':4,5]pyrazino[2,1-b][1,3]oxazine-6,8-dione (XIII), which further undergoes bromination using NBS to produce (4R,12aS)-9-bromo-4-methyl-7-[(phenylmethyl)oxy]-3,4,12,12a-tetrahydro-2H-pyrido[1',2':4,5]pyrazino[2,1-b][1,3]oxazine-6,8-dione (XIV). The bromo Compound (XIV) is condensed with 2,4-difluorobenzylamine (IV) in the presence of Tetrakis(triphenylphosphine)palladium (Pd(PPh$_3$)$_4$) to produce benzyloxy Dolutegravir (XI), which is hydrogenated in the presence of Pd/C to produce Dolutegravir (I).

The Process is as Shown in Scheme-II Below:

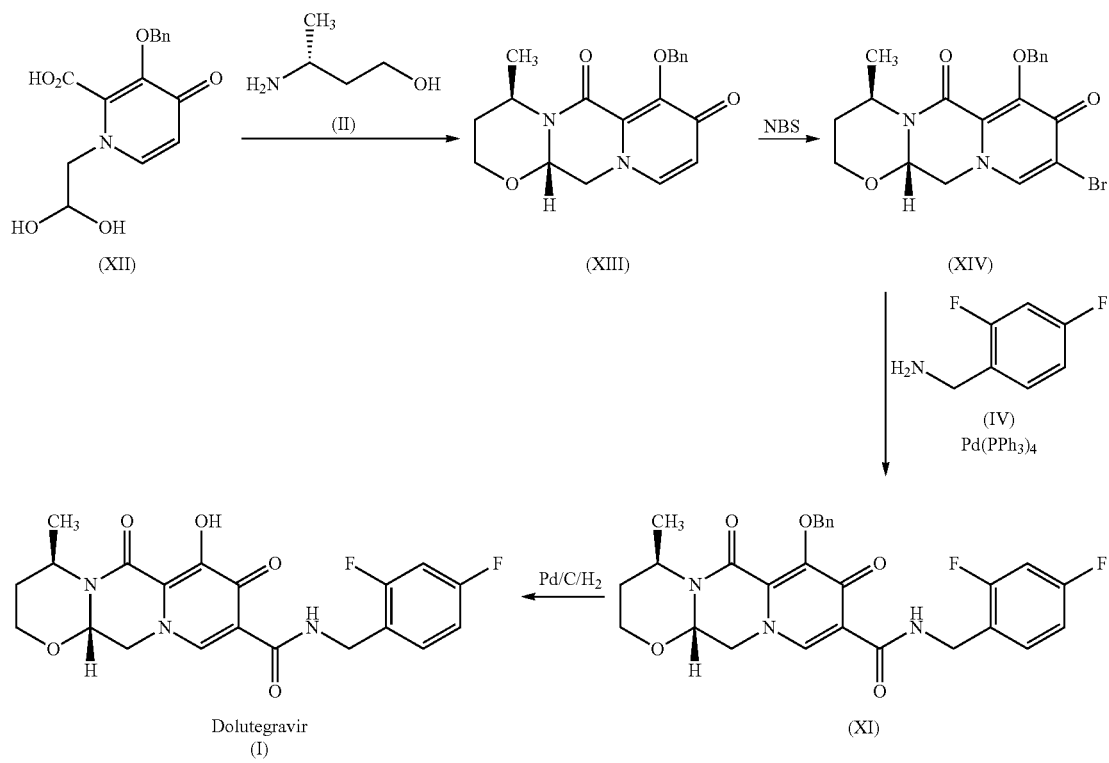

The major disadvantage with the above prior art process of preparing Dolutegravir is the use of expensive reagent tetrakis(triphenylphosphine)palladium (Pd(PPh₃)₄) in coupling step. Use of this reagent on industrial scale is not preferred, which makes the process more expensive.

WO 2011/119566 discloses another variant process for the preparation of Dolutegravir. This process involves the reaction of 1-(2,2-dimethoxyethyl)-5-methoxy-6-(methoxycarbonyl)-4-oxo-1,4-dihydropyridine-3-carboxylic acid (XV) with acetic acid in presence of methane sulfonic acid to produce 5-methoxy-6-(methoxycarbonyl)-4-oxo-1-(2-oxoethyl)-1,4-dihydropyridine-3-carboxylic acid (XVI), which is further condensed with (R)-3-amino-1-butanol (II) to produce (4R,12aS)-7-methoxy-4-methyl-6,8-dioxo-3,4,6,8,12,12a-hexahydro-2H-pyrido[1',2':4,5]pyrazino[2,1-b][1,3]-oxazine-9-carboxylic acid (XVII). This acid Compound XVII is acylated with 2,4-difluorobenzylamine (IV) in the presence of carbonyldiimidazole (CDI) to produce methoxy Dolutegravir (XVIII), which is demethylated in the presence of lithium bromide (LiBr) to produce Dolutegravir (I).

The Process is as Shown in Scheme-III Below:

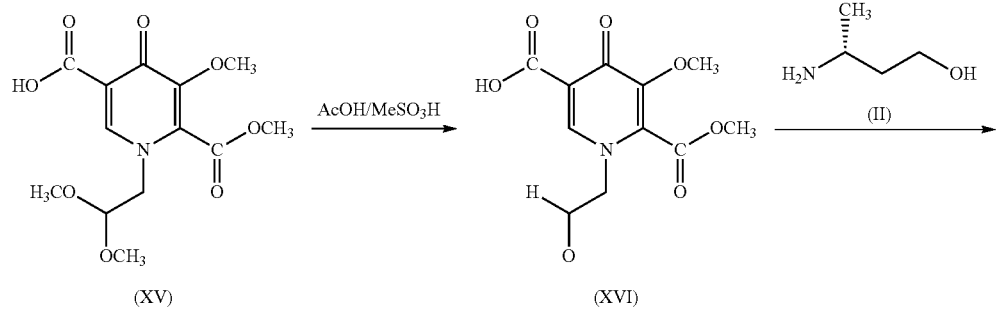

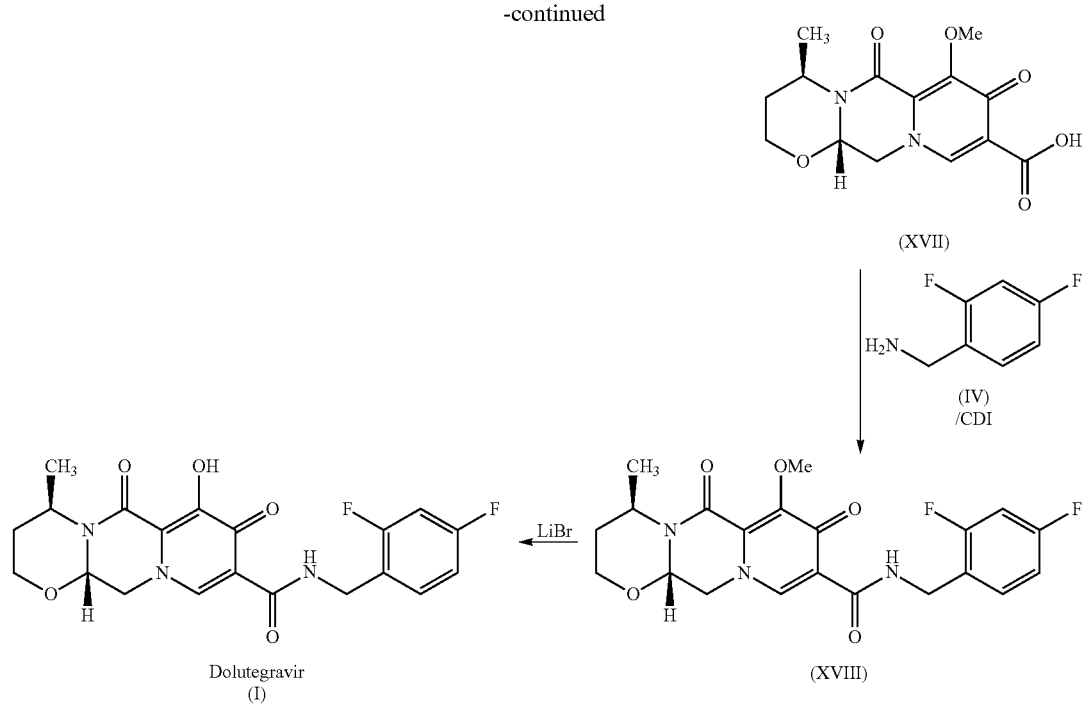

The major disadvantage of the above prior art process of preparing Dolutegravir is the use of expensive and highly moisture sensitive reagent, 1,1-carbonyldiimidazole (CDI), during acylation. Use of this reagent on industrial scale is not preferred due to anhydrous conditions required in the process.

(R)-3-Amino-1-butanol (II) is a key precursor used in the preparation of Dolutegravir (I).

*Journal of Organic Chemistry* 1977, 42(9), 1650-1652 reported a process for the preparation of (R)-3-amino-1-butanol (II) by reacting ethyl crotonate (XIX) with (−)-1-(S)-phenylethylamine (XX) to produce ethyl-3(R)—N-[1(S)-methylbenzyl]amino butyrate (XXI), which is further undergoes reduction with LiAlH$_4$ to produce 3(R)—N-[1(S)-methylbenzyl]aminobutan-1-ol (XXII). Compound (XXII) is further hydrogenating with Pd/C in ethanol to produce (R)-3-amino-1-butanol (II).

The Process is as Shown in Scheme-IV Below:

Scheme-IV

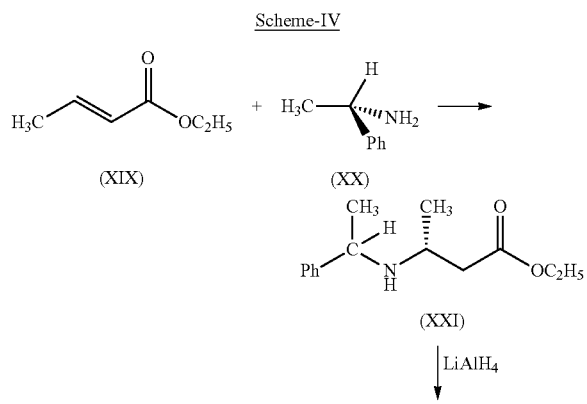

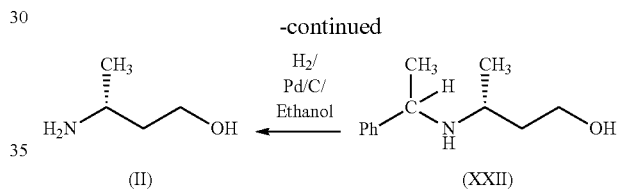

The major disadvantage of above process is that it involves large number of steps for the manufacture of (R)-3-amino-1-butanol (II). In the chemical synthesis, the number of steps is not advisable for the commercialization of the product. The number of steps is more in a chemical process means the lowering of the overall yield and the time cycle of the production is more. This does not make the suitable chemical process.

U.S. Pat. No. 8,288,575 discloses a process for the preparation of (R)-3-amino-1-butanol (II), wherein methyl (R)-3-aminobutanoate (XXIII) is hydrogenated using ruthenium complex in a solvent.

The Process is as Shown in Scheme-V Below:

Scheme-V

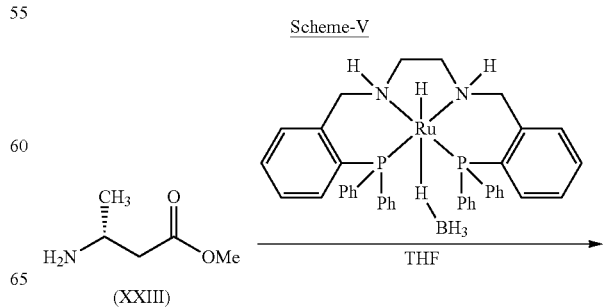

-continued

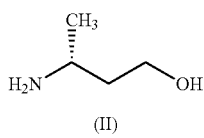

(II)

The major disadvantage with the above process is that the sensitivity and the use of more expensive catalyst such as ruthenium complex, which is not easier to handle on commercial scale, and this process is not suitable for commercial scale production of (R)-3-amino-1-butanol (II).

US 2011/0275855 A1 discloses a process for the resolution of (R,S)-3-amino-1-butanol (XXV), wherein racemic 3-amino-1-butanol undergoes resolution with (S)-mandelic acid in the presence of an acid different from (S)-mandelic acid to produce (R)-3-amino-1-butanol (S)-mandelic acid salt (IIc), which is further neutralized to produce (R)-3-amino-1-butanol (II).

The Process is as Shown in Scheme-VI Below:

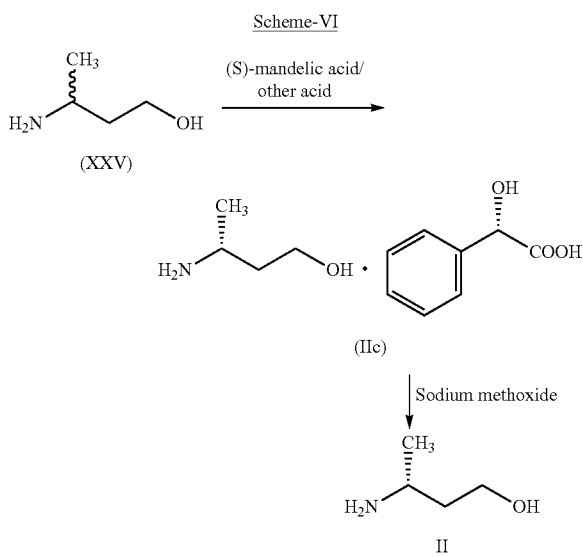

The major disadvantage with the above process is that it involves longer process time, low product yields.

However, there is always a need for alternative preparative routes, which for example, involve fewer steps, use reagents that are less expensive and/or easier to handle, consume smaller amounts of reagents, provide a higher yield of product, have smaller and/or more eco-friendly waste products, and/or provide a product of higher purity.

The present invention is related to a process for the preparation of pure Dolutegravir (I), wherein optically active acid addition salt of (R)-3-amino-1-butanol (II) is directly condensed with 5-methoxy-6-(methoxycarbonyl)-4-oxo-1-(2-oxoethyl)-1,4-dihydropyridine-3-carboxylic acid (XVI) instead of condensing with free base of (R)-3-amino-1-butanol (II).

The present invention is also related to a process for the preparation of pure Dolutegravir (I), wherein, inexpensive and easily handling condensing reagents in the condensation of (4R,12aS)-7-methoxy-4-methyl-6,8-dioxo-3,4,6,8,12,12a-hexahydro-2H-pyrido[1',2':4,5]pyrazino[2,1-b][1,3]oxazine-9-carboxylic acid (XVII) with 2,4-difluorobenzylamine (IV).

The present invention is also relates to a process for the preparation of pure (R)-3-amino-1-butanol (II), wherein 4-hydroxy-2-butanone oxime (XXIV) is subjected to hydrogenation to produce (R,S)-3-amino-1-butanol (XXV), which is further undergoes resolution using D-tartaric acid, followed by de-salting to produce (R)-3-amino-1-butanol (II).

OBJECTIVE OF THE INVENTION

The main embodiment of the present invention is to provide a simple, cost effective process for the preparation of Dolutegravir (I) with high purity and good yield on commercial scale.

Another embodiment of the present invention provides, (R)-3-amino-1-butanol (D)-tartarate (IIb), a process for its preparation and its conversion to Dolutegravir (I).

Another embodiment of the present invention is to provide a simple, cost effective process for the preparation of (R)-3-amino-1-butanol (II) with high purity and good yield on commercial scale.

(R)-3-Amino-1-butanol (II) is a key precursor used in the preparation of Dolutegravir (I).

SUMMARY OF THE INVENTION

Accordingly, in one embodiment, the present invention provides (R)-3-Amino-1-butanol (D)-tartarate (IIb).

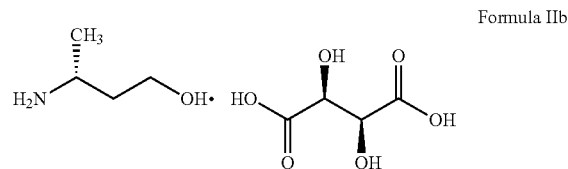

Formula IIb

In another embodiment, the present invention provides, a process for the preparation of Dolutegravir (I), by using a compound comprises (R)-3-amino-1-butanol (D)-tartarate (IIb).

In another embodiment, the present invention provides, a process for the preparation of (R)-3-amino-1-butanol (D)-tartrate salt (IIb),

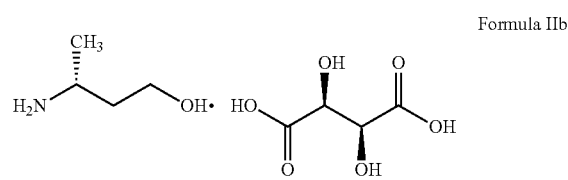

Formula IIb which comprises, treating (R,S)-3-amino-1-butanol (XXV)

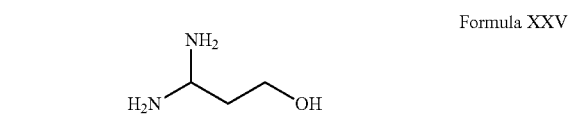

Formula XXV with (D)-tartaric acid to produce (R)-3-amino-1-butanol (D)-tartrate salt (IIb).

In another embodiment, the present invention provides an improved process for the preparation of Dolutegravir (I) or pharmaceutically acceptable salts thereof, Formula I

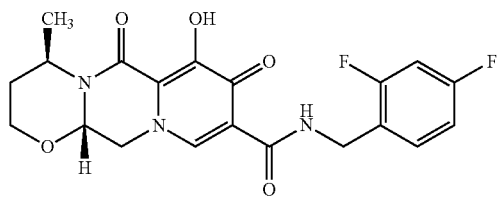

which comprises:

(i) reacting 5-methoxy-6-(methoxycarbonyl)-4-oxo-1-(2-oxoethyl)-1,4-dihydro pyridine-3-carboxylic acid (XVI), Formula XVI

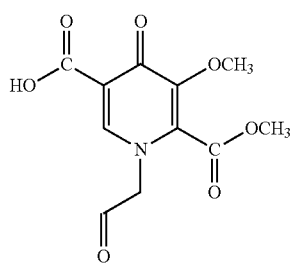

with an optically active acid addition salt of (R)-3-amino-1-butanol (IIa),

Formula IIa

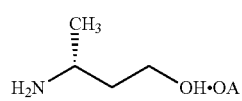

wherein, OA refers optically active acid, to produce (4R,12aS)-7-methoxy-4-methyl-6,8-dioxo-3,4,6,8,12,12a-hexahydro-2H-pyrido[1',2':4,5]pyrazino[2,1-b][1,3]oxazine-9-carboxylic acid (XVII), Formula XVII

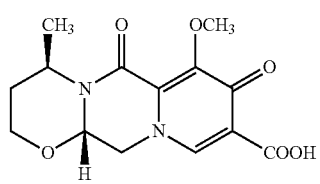

(ii) converting the compound (XVII) to Dolutegravir (I) or pharmaceutically acceptable salts thereof.

In another embodiment, the present invention provides a process for the preparation of Dolutegravir (1) or pharmaceutically acceptable salts thereof, which comprises:

(i) condensing (4R,12aS)-7-methoxy-4-methyl-6,8-dioxo-3,4,6,8,12,12a-hexa hydro-2H-pyrido[1',2':4,5]pyrazino[2,1-b][1,3]oxazine-9-carboxylic acid (XVII), Formula XVII

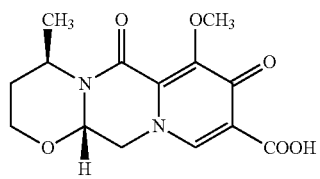

with 2,4-difluorobenzylamine (IV),

Formula IV

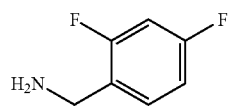

in the presence of a coupling agent to produce methoxy Dolutegravir (XVIII),

Formula XVIII

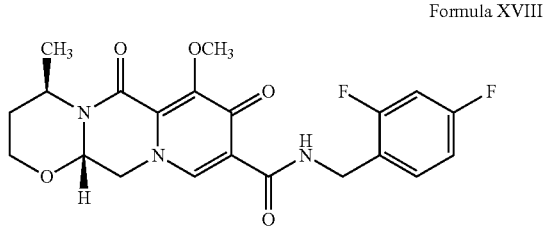 [SMILES: COc1c2n(cc(C(=O)NCc3ccc(F)cc3F)c1=O)C[C@@H]1OCC[C@@H](C)N1C2=O]

(ii) de-methylating the compound (XVIII) to produce Dolutegravir (I), or pharmaceutically acceptable salts thereof.

In yet another embodiment, the present invention also provides an improved process for the preparation of (R)-3-amino-1-butanol (II), Formula II

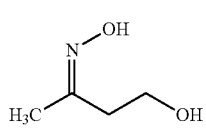

which comprises:

(i) hydrogenating 4-hydroxy-2-butanone oxime (XXIV),

Formula XXIV

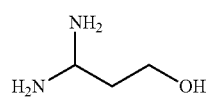

to produce (R,S)-3-amino-1-butanol (XXV),

Formula XXV

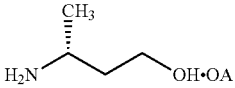

(ii) treating the compound (XXV) with optically active carboxylic acid to produce (R)-3-amino-1-butanol optically active salt (IIa), Formula IIa

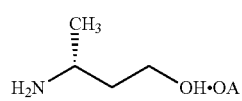

wherein, OA refers optically active acid, (iii) optionally, converting the compound (IIa) to (R)-3-amino-1-butanol (II).

DETAILED DESCRIPTION OF THE INVENTION

In one embodiment, a process for the preparation of Dolutegravir (I) comprises: condensing 5-methoxy-6-(methoxycarbonyl)-4-oxo-1-(2-oxoethyl)-1,4-dihydropyridine-3-carboxylic acid (XVI) with optically active acid addition salt of (R)-3-amino-1-butanol (IIa) in the presence of a base to produce (4R,12aS)-7-methoxy-4-methyl-6,8-dioxo-3,4,6,8,12,12a-hexahydro-2H-pyrido[1',2':4,5]pyrazino[2,1-b][1,3]oxazine-9-carboxylic acid (XVII).

The optically active acid addition salt of (R)-3-amino-1-butanol (IIa) comprises tartaric acid, dibenzoyltartaric acid, mandelic acid, camphoric acid, camphorsulfonic acid, p-hydroxymandelic acid, p-Cl-mandelic acid, phenoxypropionic acid, p-hydroxyphenoxypropionic acid or lactic acid.

The base is alkali salt of $C_1$-$C_6$ carboxylic acid comprises sodium formate, potassium formate, sodium acetate, potassium acetate or mixture thereof; inorganic base comprises sodium hydroxide, sodium carbonate, sodium bicarbonate, potassium hydroxide, potassium carbonate, potassium bicarbonate or mixture thereof.

After completion of the reaction, reaction mass is concentrated and acidified with inorganic acid or organic acid comprises hydrochloric acid, sulfuric acid, formic acid, acetic acid, methane sulfonic acid or mixture thereof; and extracted with an organic solvent comprises methylene chloride, toluene and ethyl acetate. The said organic layer is concentrated and treated with an organic solvent which is alcohol, ester, ether, hydrocarbon, ketone or mixture thereof comprises methanol, ethanol, isopropanol, ethyl acetate, acetone, toluene, tetrahydrofuran to produce compound (XVII).

The compound (XVII) obtained by the above invention is used as such without isolation in the reaction to prepare Dolutegravir (I).

The compound (XVII) obtained by the above invention is isolated by conventional methods.

In another embodiment, the process comprises: condensing (4R,12aS)-7-methoxy-4-methyl-6,8-dioxo-3,4,6,8,12,12a-hexahydro-2H-pyrido[1',2':4,5]pyrazino[2,1-b][1,3]oxazine-9-carboxylic acid (XVII) with 2,4-difluorobenzylamine (IV) in presence of a coupling agent to produce methoxy Dolutegravir (XVIII).

The coupling agent other than carbonyldiimidazole (CDI) comprises isobutyl chloroformate, pivaloyl chloride, o-benzotriazole-1-yl-1,1,3,3-tetramethyluronium tetrafluoroborate (TBTU), 2-(1H-benzotriazole-1-yl)-1,1,3,3-tetramethyluronium (HBTU), benzotriazole-1-yl-oxy-tris(dimethylamino)phosphonium (BOP), benzotriazole-1-yl-oxy-tris-(pyrrolidino)phosphonium (PyBOP), bromo-tris-pyrrolidino-phosphoniumhexaflurophosphate (PyBrOP), tris(pyroolidino)phosphonium hexaflurophosphate (pyCOP), ethyl cyanoglyoxylate-2-oxime (Oxyma Pure), O-(6-chloro-1-hydrocibenzotriazol-1-yl)-1,1,3,3-tetramethyluronium tetrafluoroborate (TCTU), 2-(1H-7-azabenzotriazol-1-yl)-1,1,3,3-tetramethyl uronium hexafluorophosphate (HATU) or 1-cyano-2-ethoxy-2-oxoethydenminooxy)dimethylamino-morpholion-carbenium hexafluorophosphate (COMU) or mixture thereof.

The reaction is carried out in presence of an organic base comprises N-methylmorpholine, triethylamine, diisopropylethylamine, N,N'-dimethylpiperazine, N-methylpiperidine, pyridine or mixture thereof; in an organic solvent comprises methylene chloride, ethyl acetate, tetrahydrofuran, dimethyl formamide, toluene, acetonitrile, acetone or mixture thereof.

The reaction is carried out at a temperature of −30 to 80° C. After completion of the condensation reaction the reaction mass comprises methoxy Dolutegravir (XVIII) is treated with an organic acid comprises acetic acid or inorganic acid comprises hydrochloric acid, methanesulfonic acid, sulfuric acid and toluene sulfonic acid or mixture thereof; followed by treating with aqueous alkali base comprises sodium carbonate, sodium bicarbonate, potassium carbonate, potassium bicarbonate.

The methoxy Dolutegravir (XVIII) obtained by the above invention is used as such without isolation in the reaction to prepare Dolutegravir (I).

The methoxy Dolutegravir (XVIII) obtained by the above invention is isolated by conventional methods.

In another embodiment, the process comprises: de-methylating methoxy Dolutegravir (XVIII) using a Lewis acid to produce Dolutegravir (I).

The Lewis acid is slat of magnesium comprises magnesium chloride, magnesium bromide or magnesium iodide; Lithium comprises lithium chloride, lithium bromide or lithium iodide in an organic solvent comprises acetonitrile, isopropanol, ethanol, tetrahydrofuran, dimethylformamide (DMF), dimethylsulfoxide (DMSO) or mixture thereof.

The reaction is carried out at a temperature of 10° C. to about 75° C., preferably in the range of 30° C. to 65° C. After completion of the reaction, the reaction mass is acidified with an organic acid or an inorganic acid to produce Dolutegravir (I), which is isolated by conventional methods.

Dolutegravir (I) is purified by known methods, for example by dissolving in a solvent comprises methanol, ethanol, isopropanol, ethyl acetate, methylene chloride, hexane, heptane, cyclohexane, acetone, THF, water or mixture thereof; and precipitating pure Dolutegravir by cooling the solution or by adding an anti solvent.

In another embodiment, Dolutegravir (I) is converted to its pharmaceutically acceptable salt by treating Dolutegravir (I) with an appropriate acid or base in presence of a solvent comprises methanol, ethanol, isopropanol, THF, ethyl acetate, acetone, acetonitrile hexane, heptane, cyclohexane, methylene chloride or mixture thereof.

Pharmaceutically acceptable salts of Dolutegravir (I) include basic salts comprises alkali metal salts selected from sodium, Lithium, potassium salts; alkaline-earth metal salts selected from calcium, magnesium salts; ammonium salts; aliphatic amine salts selected from trimethylamine, triethylamine, dicyclohexylamine, ethanolamine, diethanolamine, triethanolamine or procaine salts; aralkyl amine salts selected from N,N-dibenzylethylenediamine salts; heterocyclic aromatic amine salts selected from pyridine salts, picoline salts, quinoline salts or isoquinoline salts; quaternary ammonium salts selected from tetramethylammonium salts, tetraethylammonium salts, benzyltrimethylammonium salts, benzyltriethylammonium salts, benzyltributylammonium salts, methyltrioctylammonium salts or tetrabutylammonium salts, and basic amino acid salts selected from arginine salts or lysine salts. Acid salts include mineral acid salts selected from hydrochloride, sulfates salts, nitrate salts, phosphates salts, carbonates salts, hydrogencarbonates or perchlorate; organic acid salts selected from acetates, propionates, lactates, maleates, fumarates, tartaric acid salts, malates, citrates salts, ascorbates, formic acid; sulfonates such as methanesulfonates, isethionates, benzenesulfonates, or p-toluenesulfonates; and acidic amino acid salts selected from aspartates or glutamates.

The base is alkali metal hydroxide comprises lithium hydroxide, sodium hydroxide, potassium hydroxide, alkaline-earth metal hydroxide comprises calcium hydroxide, magnesium hydroxide; ammonium hydroxide; aliphatic amine base comprises trimethylamine, triethylamine, dicyclohexylamine, ethanolamine, diethanolamine, triethanolamine or procaine; aralkyl amine comprises N,N-dibenzylethylenediamine; heterocyclic aromatic amine comprises pyridine, picoline, quinoline or isoquinoline; quaternary ammonium base comprises tetramethylammonium chloride, tetraethylammonium bromide, benzyltrimethylammonium bromide, benzyltriethylammonium bromide, benzyltributylammonium bromide, methyltrioctylammonium bromide or tetrabutylammonium bromide, and basic amino acid comprises arginine, lysine or mixture thereof.

ethyl]amino}-2-[(methyloxy)acetyl]-2-propenoate) (XXX). The compound (XXX) is contacted with dimethyl ethanedioate in presence of alkali metal alkoxide to produce dimethyl-1-(2,2-dimethoxyethyl)-3-methoxy-4-oxo-1,4-dihydropyridine-2,5-dicarboxylate (XXXI), which is selectively hydrolyzed with a base to produce 1-[2,2-bis(methyloxy)ethyl]-5-(methyloxy)-6-[(methyloxy)carbonyl]-4-oxo-1,4-dihydro-3-pyridinecarboxylic acid (XV). The compound (XV) is treated with a catalytic amount of a strong protic acid in the presence of acetic acid in an organic solvent to produce a reaction mixture containing 5-methoxy-6-(methoxycarbonyl)-4-oxo-1-(2-oxoethyl)-1,4-dihydropyridine-3-carboxylic acid (XVI), The Process is as Shown in Scheme-VII Below:

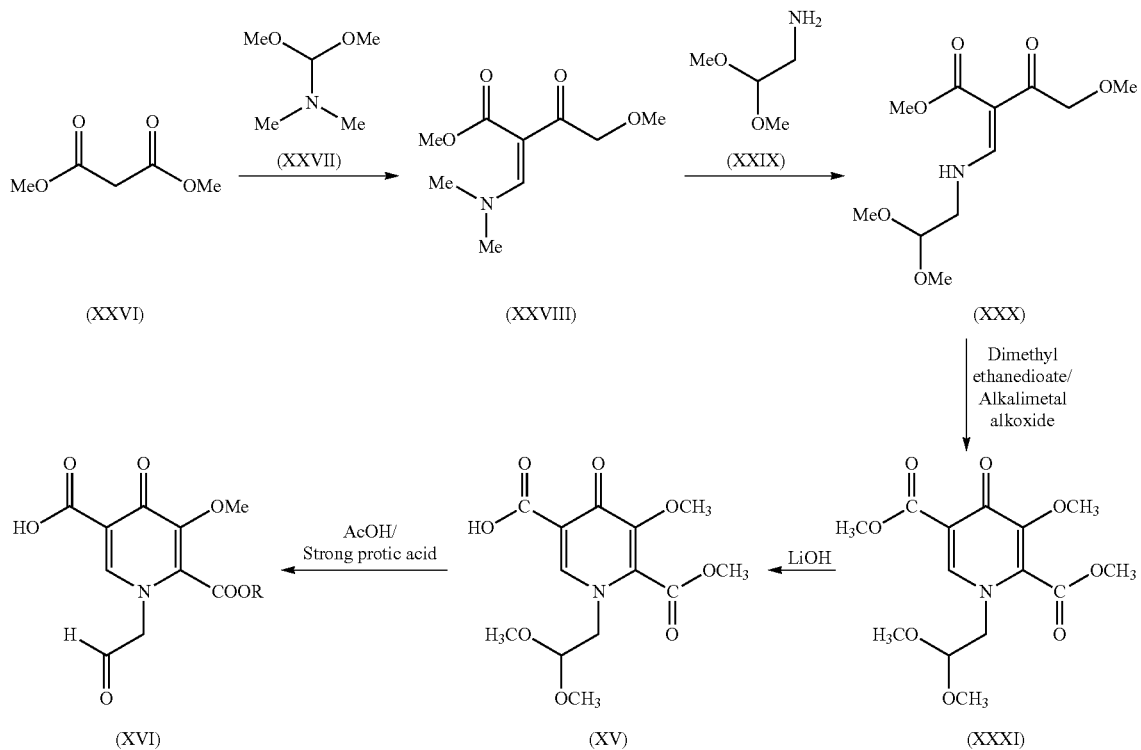

The acid is mineral acid comprises hydrochloride, hydrobromide, sulfuric acid, nitric acid, phosphoric acid, carbonic acid, or perchloric acid; organic acid comprises acetic acid, propionic acid, lactatic acid, maleic acid, fumaric acid, tartaric acid, malic acid, citric acid, ascorbic acid; sulfonic acid comprises methanesulfonic acid, benzenesulfonic aid, or p-toluenesulfonates; and acidic amino acid comprises aspartatic acid or glutamic acid or mixture thereof.

In another embodiment, 5-methoxy-6-(methoxycarbonyl)-4-oxo-1-(2-oxoethyl)-1,4-dihydropyridine-3-carboxylic acid (XVI) used in the present invention is prepared by reacting 4-methoxyacetoacetate (XXVI) with N,N-dimethyl-1,1-bis(methyloxy)methanamine (DMF-DMA) (XXVII) to produce methyl-2-(dimethylaminomethylene)-4-methoxy-3-oxo-butanoate(methyl-3-(dimethylamino)-2-[(methyloxy)acetyl]-2-propenoate) (XXVIII), which is reacted with aminoacetaldehyde dimethyl acetal (XXIX) to produce methyl-2-(2,2-dimethoxyethylaminomethylene)-4-methoxy-3-oxo-butanoate(methyl-3-{[2,2-bis(methyloxy)-

In another embodiment, a process for the preparation of (R)-3-amino-1-butanol (II), which is the key precursor of Dolutegravir (I).

The process comprises, hydrogenating 4-hydroxy-2-butanone oxime (XXIV) to produce (R,S)-3-amino-1-butanol (XXV). The hydrogenation step is carried out in the presence of a hydrogenation catalyst in presence of a solvent. The reaction is carried out at a temperature about 0° C. to about 150° C., preferably from 50 to 100° C. The hydrogenation is carried out in a pressure range of from atmospheric pressure to 300 bar. The reaction is preferably carried out at a pressure of from 50 to 150 bar.

The hydrogenation catalyst is palladium in the form Pd—C, Pd(OH)$_2$/C; platinum in the form PtO$_2$, and nickel in the form Ra—Ni, Urushibara nickel, rhodium complex, ruthenium complex. The solvent is methanol, ethanol, isopropanol, n-propanol, n-butanol, formic acid, acetic acid, water or the mixture thereof. The hydrogenation is carried out for a period of about 1 to 15 hrs. After completion of the reaction the reaction mixture is filtered and the filtrate is concentrated to obtain (R,S)-3-amino-1-butanol (XXV).

The resolution of (R,S)-3-amino-1-butanol (XXV) is carried out via classical chemical racemate resolution, including the use of chromatographic methods.

In another embodiment, (R,S)-3-Amino-1-butanol (XXV) is reacted with an optically active carboxylic acid in presence of a solvent to produce diastereomeric salt of (R)-3-amino-1-butanol with an optically active acid (IIa).

The reaction is carried out at a temperature of 10-50° C. For the separation via diastereomeric salts, all optically active carboxylic acids are suitable in principle, comprises tartaric acid, dibenzoyltartaric acid, mandelic acid, camphoric acid, camphorsulfonic acid, p-hydroxymandelic acid, p-Cl-mandelic acid, phenoxypropionic acid, p-hydroxyphenoxypropionic acid or lactic acid. After completion of the reaction the reaction mixture is filtered and dried to get diastereomeric salt of (R)-3-amino-1-butanol with an optically active acid (IIa).

The salt formation is carried out in a solvent, which is hydrocarbon comprises hexane, cyclohexane, benzene or toluene; or an ether comprises MTBE, diethyl ether, dibutyl ether or THF; or an alcohol comprises methanol, ethanol, propanol, isopropanol, butanol or isobutanol or mixture thereof.

Diastereomeric salt of (R)-3-amino-1-butanol with an optically active acid (IIa) is used as such in the reaction to prepare Dolutegravir (I) or undergoes de-salification with a base in presence of a solvent to produce (R)-3-amino-1-butanol (II).

The base is alkali or alkaline earth metal hydroxides comprises lithium hydroxide, sodium hydroxide, potassium hydroxide, calcium hydroxide, aluminum hydroxide, magnesium hydroxide, zinc hydroxide, an alkali metal alkoxide comprises sodium methoxide, sodium ethoxide and the like, an alkali metal carbonate comprises sodium carbonate or potassium carbonate; an alkali metal hydrogencarbonate comprises sodium hydrogencarbonate or potassium hydrogencarbonate; an alkali metal hydride comprises sodium hydride, potassium hydride and the like or mixture thereof. The solvent used in the above reaction is comprises ethanol, methanol, isopropanol, n-propanol, acetone, ethyl acetate, methyl ethyl ketone, acetonitrile, N,N-dimethylformamide and dimethyl sulfoxide, carbon tetrachloride, chloroform, cyclohexane, 1,2-dichloroethane, dichloromethane, diethyl ether, dimethyl formamide, ethyl acetate, heptane, hexane, methyl-tert-butyl ether, toluene or mixture thereof. After completion of the reaction, filter the reaction mass and the filtrate is distilled to obtain (R)-3-amino-1-butanol (II).

In another embodiment, the present invention provides (R)-3-Amino-1-butanol (D)-tartarate (IIb).

In another embodiment, the present invention provides, a process for the preparation of Dolutegravir (I), by using a compound comprises (R)-3-amino-1-butanol (D)-tartarate (IIb).

In another embodiment, the present invention provides a process for the preparation of (R)-3-amino-1-butanol (D)-tartarate (IIb).

The reaction comprises, the resolution of (R,S)-3-amino-1-butanol (XXV) using D-(−) tartaric acid in presence of a solvent to produce (R)-3-amino-1-butanol tartarate salt (IIb).

The reaction is carried out at a temperature of 10-50° C. The salt formation is carried out in a solvent, which is hydrocarbon comprises hexane, cyclohexane, benzene or toluene; or an ether comprises MTBE, diethyl ether, dibutyl ether or THF; or an alcohol comprises methanol, ethanol, propanol, isopropanol, butanol or isobutanol or mixture thereof. After completion of the reaction the reaction mixture is filtered and dried to get (R)-3-amino-1-butanol tartarate salt (IIb).

(R)-3-Amino-1-butanol tartarate salt (IIb) is used as such in the reaction to prepare Dolutegravir (I) or undergoes de-salification with a base in presence of a solvent to produce (R)-3-amino-1-butanol (II).

The base is alkali or alkaline earth metal hydroxides comprises lithium hydroxide, sodium hydroxide, potassium hydroxide, calcium hydroxide, aluminum hydroxide, magnesium hydroxide, zinc hydroxide, an alkali metal alkoxide comprises sodium methoxide, sodium ethoxide and the like, an alkali metal carbonate comprises sodium carbonate or potassium carbonate; an alkali metal hydrogencarbonate comprises sodium hydrogencarbonate or potassium hydrogencarbonate; an alkali metal hydride comprises sodium hydride, potassium hydride and the like or mixture thereof. The solvent used in the above reaction is comprises ethanol, methanol, isopropanol, n-propanol, acetone, ethyl acetate, methyl ethyl ketone, acetonitrile, N,N-dimethylformamide and dimethyl sulfoxide, carbon tetrachloride, chloroform, cyclohexane, 1,2-dichloroethane, dichloromethane, diethyl ether, dimethyl formamide, ethyl acetate, heptane, hexane, methyl-tert-butyl ether, toluene or mixture thereof. After completion of the reaction, filter the reaction mass and the filtrate is distilled to obtain (R)-3-amino-1-butanol (II).

In another embodiment, 4-hydroxy-2-butanone oxime (XXIV) used in the present invention is prepared by reacting acetone with formaldehyde in presence of a base in a solvent to produce 4-hydroxy-2-butanone (XXXII). The compound (XXXII) is reacted with hydroxylamine hydrochloride in presence of a solvent to produce 4-hydroxy-2-butanone oxime (XXIV).

The reaction is carried out at a temperature of 5-90° C. The base used in the above reaction comprises alkali or alkaline earth metal hydroxides. The solvent is organic solvent comprises acetone, ethyl acetate, methyl ethyl ketone, acetonitrile, N,N-dimethylformamide and dimethyl sulfoxide, citric acid or mixture thereof.

After completion of the reaction, the solvent is distilled by rotary evaporator at 40° C. and crude compound (XXVI) obtained is subjected to fractional distillation to produce 4-hydroxy-2-butanone (XXVI).

4-Hydroxy-2-butanone (XXVI) obtained is reacted with hydroxylamine hydrochloride in presence of a solvent to produce 4-hydroxy-2-butanone oxime (XXIV).

The reaction is carried out at a temperature of 0-35° C. The solvent is methanol, ethanol and isopropanol or mixture thereof. pH of the reaction mixture is adjusted to 4.0 to 6.0 using a base comprises aqueous sodium hydroxide, potassium hydroxide or mixture thereof. After, completion of the reaction the reaction mass is filtered and the filtrate is distilled out to obtain 4-hydroxy-2-butanone oxime (XXIV).

The Process is as Shown in Scheme-VIII Below:

Scheme-VIII

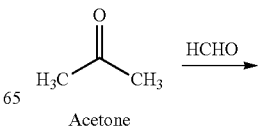

Acetone

-continued

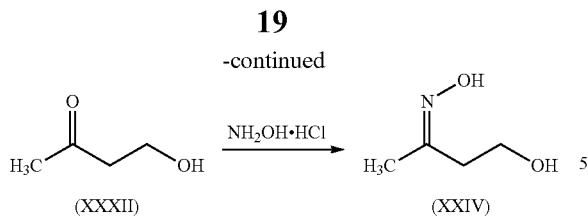

The following examples illustrate the nature of the invention and are provided for illustrative purposes only and should not be construed to limit the scope of the invention.

EXAMPLES

Example-1

Process for the Preparation of Dolutegravir

Step-i: Preparation of (R)-3-amino-1-butanol tartarate salt

D-(+) Tartaric acid (12.7 g, 0.085 mol) was added in to a solution of (R,S)-3-amino-1-butanol (7.5 g, 0.084 mol) in methanol (100 ml) at 40° C. The reaction mixture was stirred for about 1 hour at 35-40° C. and the reaction mass was cooled to 0-5° C. and maintained for 30-40 minutes. The obtained solid was filtered and washed with chilled methanol (10 ml) at 0-5° C. The solid was dried to get (R)-3-amino-1-butanol tartarate salt (8.0 g, 40%).

Step-ii: Preparation of (4R,12aS)-7-methoxy-4-methyl-6,8-dioxo-3,4,6,8,12,12a-hexahydro-2H-pyrido[1',2':4,5]pyrazino[2,1-b][1,3]oxazine-9-carboxylic acid (XVII)

1-[2,2-Bis(methyloxy)ethyl]-5-(methyloxy)-6-[(methyloxy)carbonyl]-4-oxo-1,4-dihydro-3-pyridinecarboxylic acid (XV) (100 g; 0.3175 moles) was suspended in acetonitrile (800 ml) and heated to 80-82° C. A mixture of acetic acid (95.25 g), methanesulfonic acid (9.14 g; 0.09525 moles) and acetonitrile (200 ml) were added to the slurry at 80-82° C. The reaction mass was continued at 80-82° C. to complete the reaction. After completion of the reaction, anhydrous sodium acetate (65 g) and (R)-3-amino-1-butanol tartrate salt (79.68 g; 0.3334 moles) were added at 20-25° C. and stirred at 60-65° C. to complete the reaction.

The reaction mass was concentrated and acidified with 1N aqueous hydrochloric acid (750 ml) and extracted with methylene chloride (1500 ml) at ice cold temperature. The organic layer was separated, concentrated, treated with hot methanol (350 ml) for 2 h, filtered, washed with methanol and dried to yield (4R,12aS)-7-methoxy-4-methyl-6,8-dioxo-3,4,6,8,12,12a-hexahydro-2H-pyrido[1',2':4,5]pyrazino[2,1-b][1,3]oxazine-9-carboxylic acid (XVII) (72 g; HPLC purity: 99.07%).

Step-iii: Process for the Preparation of Dolutegravir (I)

Method A:
Triethylamine (3.61 g; 0.0357 moles) was added to the suspension of (4R,12aS)-7-methoxy-4-methyl-6,8-dioxo-3,4,6,8,12,12a-hexahydro-2H-pyrido[1',2':4,5]pyrazino[2,1-b][1,3]oxazine-9-carboxylic acid (XVII) (10 g; 0.0325 moles) in methylene chloride (50 ml), and cooled to 10-15° C. Pivaloyl chloride (4.3 g; 0.0357 moles) was added to the reaction mass, and stirred at 10-15° C. for 1 h. Thereafter, 2,4-difluorobenzylamine (5.58 g; 0.0389 moles) was added at 10-15° C. and then warmed to 20-25° C. to complete the reaction.

After completion of the reaction, 1N aqueous hydrochloric acid (20 ml) was added, organic layer was separated, washed with 5% w/w aqueous sodium bicarbonate solution (10 ml) followed by 15% w/w aqueous sodium chloride solution (10 ml) and concentrated. To the concentrated mass, acetonitrile (100 ml) and Lithium bromide (5.08 g; 0.0584 moles) were added and heated to 65-70° C. for 3 h to complete the reaction.

After completion of the reaction, the reaction mass was acidified with 5N aqueous hydrochloric acid (40 ml), concentrated to about 50 ml and DM water was added to crystallize the product at 20-25° C. The slurry was stirred for 2 h, filtered, washed with DM water and dried to yield (4R,12aS)—N-(2,4-difluorobenzyl)-7-hydroxy-4-methyl-6,8-dioxo-3,4,6,8,12,12a,-hexahydro-2H-pyrido[1',2':4,5]pyrazino[2,1-b][1,3]oxazine-9-carboxamide (I) (11.5 g, HPLC purity: 99.63%).

Method B:
Isobutyl chloroformate (4.65 gm, 0.03404 moles) in methylene chloride (10 ml) was added to the solution of N-methylmorpholine (3.45 gm, 0.03410 moles) and (4R,12aS)-7-methoxy-4-methyl-6,8-dioxo-3,4,6,8,12,12a-hexahydro-2H-pyrido[1',2':4,5]pyrazino-[2,1-b][1,3]oxazine-9-carboxylic acid (XVII) (10.0 gm, 0.03245 moles) in methylene chloride (60 ml) at −10 to 0° C. in about 1 h. 2,4-Difluoro benzyl amine (4.88 gm, 0.03409 moles) in methylene chloride (10 ml) was added to the cold reaction mass, and stirred at 20-30° C. for completion of reaction. After completion of reaction, the reaction mass was washed with 5% w/w aqueous sodium bicarbonate solution (20 ml), 1N hydrochloric acid (20 ml), DM water (20 ml) and concentrated.

Acetonitrile (120 ml) and lithium bromide (4.8 gm, 0.05516 moles) were added to the concentrated mass, and stirred at 70-80° C. for 3 h to complete the reaction. After completion of reaction, the reaction mass was acidified with 5N aqueous hydrochloric acid (40 ml) and concentrated to about 50 ml. DM Water (100 ml) was added to the concentrated reaction mass and stirred for 2 h at 25-30° C. to crystallize the product. The product was filtered, washed with DM Water (50 ml) and dried to yield Dolutegravir (I) (10.7 gm, HPLC purity: 99.60%).

Example-2

Process for the Preparation of Dolutegravir (I)

(4R,12aS)—N-(2,4-difluorobenzyl)-7-methoxy-4-methyl-6,8-dioxo-3,4,6,8,12,12a,-hexahydro-2H-pyrido[1',2':4,5]pyrazino[2,1-b][1,3]oxazine-9-carboxamide (XVIII) (2 g, 0.0046 moles) was suspended in isopropyl alcohol (20 ml) and lithium bromide (0.8 g, 0.00924 moles) was added and stirred at 70-80° C. for 15 h to complete the reaction. After completion of reaction the reaction mass was acidified with 5N aqueous hydrochloric acid (5 ml) and concentrated. DM Water (20 ml) was added to the concentrated mass and stirred at 25-30° C. to crystallize the product. The product was filtered, washed with DM Water and dried to yield Dolutegravir (1) (1.5 g, HPLC purity: 97.93%).

Example 3

Process for the Preparation of (R)-3-amino-1-butanol (I)

Step-i: Preparation of 4-hydroxy-2-butanone

The pH of the formaldehyde solution (79 ml, 1.0 mol) was adjusted to 10 with 10% aqueous sodium hydroxide solution (~20 ml) and this solution was added into a mixture of acetone (174 g, 3.0 moles) and 10% citric acid solution (5.0 ml) at 80° C. for about 3 hours. The reaction mixture was stirred for one hour at 80° C. The solvent was distilled by rotary evaporator at 40° C. and crude obtained was subjected to fractional distillation to produce 4-hydroxy-2-butanone (50 g) as a colorless liquid.

Step-ii: Preparation of 4-hydroxy-2-butanone oxime

Hydroxylamine hydrochloride (9.5 g, 0.136 mol) was added to a solution of 4-hydroxy-2-butanone (10 g, 0.113 mol) in methanol (100 ml) at 0-5° C. The reaction mixture was stirred with continuous pH adjustment to 4.0-6.0 using 40% aqueous sodium hydroxide solution (~15 ml) for about one hour at 0-5° C. On completion of the reaction by thin layer chromatography, reaction mass was filtered and the cake was washed with methanol (10 ml) at 0-5° C. The filtrate was distilled by rotary evaporator to obtain 4-hydroxy-2-butanone oxime (10.5 g, 90%) as a pale yellow syrup.

Step-iii: Preparation of (R,S)-3-amino-1-butanol

4-Hydroxy-2-butanone oxime was dissolved (10.0 g, 0.097 mol) in methanol (100 ml). 8.0 ml of Raney nickel was added to the reaction mixture and hydrogenated under 10 kg/cm$^2$ pressure at 40-45° C. for overnight. On completion of the reaction by thin layer chromatography, the reaction mixture was filtered on celite bed under nitrogen atmosphere. The filtrate was concentrated by rotary evaporator to obtain (R,S)-3-amino-1-butanol (7.8 g, 90%) as a thick pale yellow liquid.

Step-iv: Preparation of (R)-3-amino-1-butanol tartarate salt

D-(+) Tartaric acid (12.7 g, 0.085 mol) was added in to a solution of (R,S)-3-amino-1-butnaol (7.5 g, 0.084 mol) in methanol (100 ml) at 40° C. The reaction mixture was stirred for about 1 hour at 35-40° C. and the reaction mass was cooled to 0-5° C. and maintained for 30-40 minutes. The obtained solid was filtered and washed with chilled methanol (10 ml) at 0-5° C. The solid was dried to get (R)-3-amino-1-butanol tartarate salt (8.0 g, 40%).

Step-v: Preparation of (R)-3-amino-1-butanol

Method A:
Potassium carbonate (32.0 g, 0.232 mol) was added in to a solution of (R)-3-amino-1-butnaol tartarate (8.0 g, 0.033 mol) in acetonitrile (80 ml) at 40-45° C. The reaction mixture was stirred for overnight at 40-45° C. and the reaction mixture was cooled to 20-25° C. The reaction mass was filtered and the cake was washed with acetonitrile (10 ml) at 20-25° C. The filtrate was distilled by rotary evaporator to obtain (R)-3-Amino-1-butanol (2.9 g, 95%) as pale yellow syrup.

Method B:
Sodium methoxide (12.13 g; 2 eq) was added in to a solution of (R)-3-amino-1-butanol tartarate (10 g, 1 eq) in methanol (30 ml). The reaction mixture was stirred for 2 hrs at 60-65° C. The reaction mass was filtered. The filtrate was subjected to fractional distillation to get pure (R)-3-Amino-1-butanol (3.3 g, 90%) as pale yellow syrup.

We claim:
1. (R)-3-Amino-1-butanol (D)-tartarate (Formula IIb)

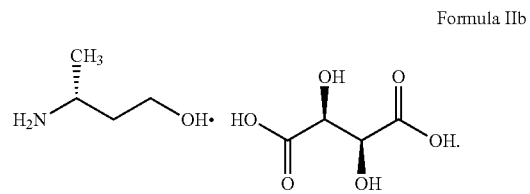

2. A process for the preparation of (R)-3-amino-1-butanol (D)-tartrate salt (Formula IIb),

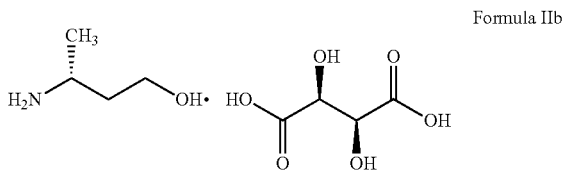

which comprises, reacting (R,S)-3-amino-1-butanol (Formula XXV)

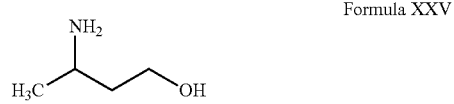

with (D)-tartaric acid to produce (R)-3-amino-1-butanol (D)-tartrate salt (Formula IIb).

3. The process according to claim 2, wherein the reaction is carried out in presence of a solvent comprising a hydrocarbon, an ether, an alcohol or mixtures thereof.

4. A process for the preparation of (R)-3-amino-1-butanol (Formula II) or optically active addition salt thereof,

which comprises:
(i) hydrogenating 4-hydroxy-2-butanone oxime (Formula XXIV),

to produce (R,S)-3-amino-1-butanol (Formula XXV),

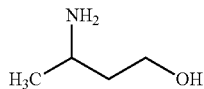

Formula XXV (ii) treating the compound (XXV) with optically active carboxylic acid to produce diastereomeric salt of (R)-3-amino-1-butanol optically active acid (Formula IIa),

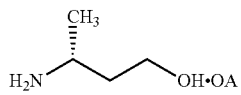

Formula IIa wherein, OA refers optically active acid, (iii) optionally, converting the compound (IIa) to (R)-3-amino-1-butanol (Formula II).

5. The process according to claim 4, wherein the hydrogenation, in step-(i) is carried out in the presence of hydrogenation catalyst in a solvent selected from the group comprising methanol, ethanol, isopropanol, n-propanol, n-butanol, formic acid, acetic acid, water or the mixture thereof.

6. The process according to claim 5, wherein the hydrogenation catalyst is selected form the group comprising palladium in the form of Pd—C, Pd(OH)$_2$/C; platinum in the form of PtO$_2$, and nickel in the form of Ra—Ni, Urushibara nickel, rhodium complex; or ruthenium complex.

7. The process according to claim 4, wherein the optically active acid is selected form the group comprising tartaric acid, dibenzoyltartaric acid, mandelic acid, camphoric acid, camphorsulfonic acid, p-hydroxymandelic acid, p-Cl-mandelic acid, phenoxypropionic acid, p-hydroxyphenoxypropionic acid or lactic acid or mixture thereof.

8. The process according to claim 4, wherein the diastereomeric salt of (R)-3-amino-1-butanol with an optically active acid (IIa) is treated with a base selected from the group comprising alkali or alkaline earth metal hydroxide, alkali metal carbonate, alkali metal hydrogencarbonate, an alkali metal hydride or mixtures thereof in presence of a solvent to convert to (R)-3-amino-1-butanol (II).

9. The process according to claim 8, wherein the solvent is selected form the group comprising methanol, ethanol, isopropanol, n-propanol, acetone, ethyl acetate, methyl ethyl ketone, acetonitrile, N,N-dimethylformamide and dimethyl sulfoxide, carbon tetrachloride, chloroform, cyclohexane, 1,2-dichloroethane, dichloromethane, diethyl ether, dimethyl formamide, ethyl acetate, heptane, hexane, methyl-tert-butyl ether, toluene or mixture thereof.

10. A process as claimed in claim 2, wherein the compound of Formula IIb is converted to Dolutgravir.

\* \* \* \* \*